United States Patent  
Montoya (10) Patent No.: US 11,826,566 B2
(45) Date of Patent: Nov. 28, 2023

(54) METHOD OF TREATING A PATIENT AND APPARATUS THEREFOR

(71) Applicant: EDGAR-INVEST MANAGEMENT GROUP INC., Pinecrest, FL (US)

(72) Inventor: Michael Montoya, Burlington (CA)

(73) Assignee: EDGAR-INVEST MANAGEMENT GROUP INC., Pinecrest, FL (US)

( * ) Notice: Subject to any disclaimer, the term of this patent is extended or adjusted under 35 U.S.C. 154(b) by 0 days.

(21) Appl. No.: 16/803,843

(22) Filed: Feb. 27, 2020

(65) Prior Publication Data

US 2022/0218992 A1 Jul. 14, 2022

Related U.S. Application Data

(60) Provisional application No. 62/821,213, filed on Mar. 20, 2019.

(51) Int. Cl.
*A61N 1/36* (2006.01)
*A61N 1/04* (2006.01)

(52) U.S. Cl.
CPC ....... *A61N 1/36034* (2017.08); *A61N 1/0428* (2013.01); *A61N 1/0452* (2013.01); *A61N 1/0456* (2013.01); *A61N 1/36003* (2013.01); *A61N 1/36021* (2013.01)

(58) Field of Classification Search
CPC .............. A61N 1/36034; A61N 1/0428; A61N 1/0452; A61N 1/0456; A61N 1/36003; A61N 1/36021

See application file for complete search history.

(56) References Cited

U.S. PATENT DOCUMENTS

| | | | | |
|---|---|---|---|---|
| 5,776,173 A | * | 7/1998 | Madsen, Jr. | A61N 1/025 607/67 |
| 6,195,585 B1 | * | 2/2001 | Karunasiri | A61N 1/37211 607/57 |
| 6,792,315 B2 | | 9/2004 | Carter et al. | |
| 8,731,657 B1 | * | 5/2014 | Shambayati | A61N 1/36031 606/42 |
| 2007/0299895 A1 | * | 12/2007 | Johnson | G06F 1/0321 708/270 |
| 2011/0082524 A1 | * | 4/2011 | Thomas | A61N 1/36034 607/72 |

(Continued)

FOREIGN PATENT DOCUMENTS

| | | |
|---|---|---|
| CA | 2780275 | 4/2011 |
| WO | WO2014/145239 A1 | 9/2014 |

*Primary Examiner* — Gary Jackson
*Assistant Examiner* — Alexander M Eisenberg
(74) *Attorney, Agent, or Firm* — MALLOY & MALLOY, P.L.; William John Eagan (57) ABSTRACT

A method and apparatus for treating a patient by generating a first series of pulses having a frequency in a range from about 1 Hz to about 5 kHz, a voltage range from 0 (zero) volts to 100 (one hundred) volts, and a duty cycle of 1% to 90%; generating a second series of pulses having a frequency in a range from 5 kHz to 50 kHz, a voltage range from 0 (zero) volts to 100 (one hundred) volts, and a duty cycle of 1% to 90%; modulating the first series of pulses and the second series of pulses into a combined waveform of pulses; and delivering the combined waveform of pulses to the skin of the patient via an electrical circuit.

15 Claims, 6 Drawing Sheets

(56) References Cited

U.S. PATENT DOCUMENTS

| | | | | |
|---|---|---|---|---|
| 2012/0226333 A1* | 9/2012 | Szeles | ............... | A61H 39/002 |
| | | | | 607/59 |
| 2016/0248455 A1* | 8/2016 | Dhanasekaran | ....... | H03G 7/007 |
| 2017/0071823 A1* | 3/2017 | Chao | ............... | A61N 1/36034 |
| 2018/0133507 A1* | 5/2018 | Malchano | ............ | A61B 5/0036 |
| 2018/0193640 A1* | 7/2018 | Murphy | ................ | A61N 1/323 |
| 2019/0209831 A1* | 7/2019 | Dernebo | .............. | A61N 1/0484 |
| 2019/0358460 A1* | 11/2019 | Alford | ................ | A61B 5/7228 |
| 2020/0155841 A1* | 5/2020 | Bhagat | ................ | A61N 1/3603 |

\* cited by examiner

METHOD OF TREATING A PATIENT AND APPARATUS THEREFOR

FIELD OF THE INVENTION

The present invention relates to a method of treating a patient and apparatus therefor, and more particularly to a method of introducing pulses to a patient through the use of an electrical muscle stimulation apparatus for treatment of the patient.

BACKGROUND OF THE INVENTION

It is well known that electrical energy, specifically pulses of electricity at various voltage levels and frequencies, can be used to heal and repair human tissue, and can even relieve undesirable and painful symptoms in a human, and even eliminate disease.

Under typical human movement, the brain sends impulses to the muscles, thereby causing them to voluntarily contract. With this in mind, prior art electrical stimulation units that are used to help heal patients in various manners. It has been found that stimulating the muscles using electrical pulses that are at least in some manner similar to the electrical impulses from the human's brain can have therapeutic effects. Accordingly, typical electrical muscle stimulation units tend to employ the use of pulses. The voltage level, frequency and duration of these pulses are based to at least some degree on the reaction and behaviour of human muscle tissue to electrical impulses received from the brain.

It has been found that the human body responds to such electrical pulses from such electrical stimulation units by sending extra blood and oxygen to the area being treated. This increased circulation is the same natural process used by the body when performing a healing function. Accordingly, such electrical stimulation units are used for pain relief, decrease of inflammation, improved circulation, recovery from injury, fighting disease, muscle conditioning, and assisting muscles to contract properly.

Various types of electrical muscle stimulation therapies are well known in the prior art.

Transcutaneous electrical nerve stimulation (TENS or TNS) involves the use of a complete range of transcutaneously applied currents used for nerve excitation, Generally, TENS is applied at high frequency (>50 Hz) with an intensity below motor contraction (sensory intensity) or low frequency (<10 Hz) with an intensity that produces motor contraction.

Neuromuscular electrical stimulation (NMES) is a non-invasive, non-addictive means of muscle rehabilitation used help return a patient to normal function quickly after an injury, surgery, or disease. NMES applies customized electrical stimulus to cause a muscle to contract.

Inferential current (IFC) electrical stimulation, also known as Interferential Therapy (IFT), helps decrease pain and improve circulation to injured tissues. The IFC/IFT works much like TENS, but the current can be easily moved and varied to target the most painful area of injury. The basic principle of IFC/IFT is to utilise the significant physiological effects of low frequency (<250 pps) electrical stimulation of nerves without the associated painful and somewhat unpleasant side effects sometimes associated with low frequency stimulation.

Iontophoresis is a type of electrical stimulation used to transdermally administer medication to a patient. Typically, an electrical current applied from about 6 volts to about 24 volts at about 10% to 90% pulsed current. The use of Iontophoresis with appropriate medication can be used to help decrease inflammation, decrease swelling, and decrease muscle spasms, among other things.

Presently, the closest known prior art to the present invention is disclosed in U.S. Pat. No. 9,302,102, issued Apr. 5, 2016, to Thomas et al. The Thomas patent discloses an electro-therapeutic stimulator that provides an output signal having a first controllable main pulse periodic-exponential signal and a second background pulse periodic-exponential signal. The main pulse signal is controllable, preferably to a digital numerical value of 1 to 500 pulses per second, to a digital, numerical value of duty cycle, and to a digital numerical value of balance. The signal is produced using a class D amplifier and with a transformer optimized for the background pulse (such as at 10 kHz) rather than for the main pulse.

It has been found that this particular electrotherapeutic stimulator does not produce a desirable waveform throughout much of its range of frequency and duty cycle due to the fact that it has used an output transformer optimised for the background pulses. It has also been found that it can produce pulses that provide current greater than a desired threshold, especially upon initial application.

Another prior art patent that is in the same area as the present invention is U.S. Pat. No. 7,499,746 issued Apr. 5, 2016, to Buhlmann et al. The Buhlmann patent discloses an automated adaptive muscle stimulation system and method that includes at least one electrode assembly adapted to deliver a muscle stimulation signal to the tissue of a user, a sensor system adapted to detect a muscle response, and an electrical stimulation device operably coupled to the at least on electrode assembly and the sensor system. The electrical stimulation device includes a control system operable to automatically diagnose at least one characteristic of a muscle from the detected muscle response and adjust at least one parameter of the muscle stimulation signal in response thereto. The device delivers an adjusted muscle stimulation signal as per the at least one parameter. The electrical stimulation device also includes a dual mode muscle stimulation system adapted to accept first and second data sets and provide first and second levels of treatment data.

It is an object of the present invention to provide a method of treating a patient and apparatus therefor.

It is an object of the present invention to provide a method of treating a patient and apparatus therefor that uses electrical pulses delivered to a patient.

It is an object of the present invention to provide a method of treating a patient and apparatus therefor that uses electrical pulses delivered to a patient, which electrical pulses comprise a first series of pulses and a second series of pulses.

It is an object of the present invention to provide a method of treating a patient and apparatus therefor that uses electrical pulses delivered to a patient, which electrical pulses comprise a first series of pulses having a frequency in a range from about 1 Hz to about 5 kHz, a voltage range from about 0 (zero) volts to about 100 (one hundred) volts, and a duty cycle of about 1% to about 90% and a second series of pulses having a frequency in a range from about 5 kHz to about 50 kHz, a voltage range from about 0 (zero) volts to about 100 (one hundred) volts, and a duty cycle of about 1 to about 90%.

It is an object of the present invention to provide a method of treating a patient and apparatus therefor that uses electrical pulses delivered to a patient, which electrical pulses comprise a first series of pulses and a second series of pulses, and adjusting the voltage of at least one of the first series of pulses and the second series of pulses based on said voltage adjustment to thereby control the output current level below a maximum threshold.

It is an object of the present invention to provide a method of treating a patient and apparatus therefor that uses electrical pulses delivered to a patient, wherein various impedance values, comparison values, and actions to be taken are displayed.

It is an object of the present invention to provide a method of treating a patient and apparatus therefor that uses electrical pulses delivered to a patient, wherein the first series of pulses and said second series of pulses are automatically adjusted based on measured impedance values.

It is an object of the present invention to provide an electrical muscle stimulation therapy apparatus.

It is an object of the present invention to provide an electrical muscle stimulation therapy apparatus, wherein the electrical muscle stimulation therapy apparatus produces a first series of pulses and a second series of pulses.

It is an object of the present invention to provide an electrical muscle stimulation therapy apparatus, wherein the electrical muscle stimulation therapy apparatus produces a first series of pulses having a frequency in a range from about 1 Hz to about 5 kHz, a voltage range from about 0 (zero) volts to about 100 (one hundred) volts, and a duty cycle of about 1% to about 90% and a second series of pulses having a frequency in a range from about 5 kHz to about 50 kHz, a voltage range from about 0 (zero) volts to about 100 (one hundred) volts, and a duty cycle of about 1% to about 90%.

It is an object of the present invention to provide an electrical muscle stimulation therapy apparatus, wherein the electrical muscle stimulation therapy apparatus produces a first series of pulses and a second series of pulses, and adjusting the voltage of at least one of the first series of pulses and the second series of pulses based on said voltage adjustment to thereby control the output current level below a maximum threshold.

It is an object of the present invention to provide an electrical muscle stimulation therapy apparatus, wherein various impedance values, comparison values, and actions to be taken are displayed.

It is an object of the present invention to provide an electrical muscle stimulation therapy apparatus, wherein the electrical muscle stimulation therapy apparatus produces a first series of pulses and said second series of pulses that are automatically adjusted based on measured impedance values.

It is an object of the present invention to provide an electrical muscle stimulation therapy method.

It is an object of the present invention to provide an electrical muscle stimulation therapy method, wherein the electrical muscle stimulation therapy method produces a first series of pulses and a second series of pulses.

It is an object of the present invention to provide an electrical muscle stimulation therapy method, wherein the electrical muscle stimulation therapy method produces a first series of pulses having a frequency in a range from about 1 Hz to about 5 kHz, a voltage range from about 0 (zero) volts to about 100 (one hundred) volts, and a duty cycle of about 1% to about 90% and a second series of pulses having a frequency in a range from about 5 kHz to about 50 kHz, a voltage range from about 0 (zero) volts to about 100 (one hundred) volts, and a duty cycle of about 1% to about 90%.

It is an object of the present invention to provide an electrical muscle stimulation therapy method, wherein the electrical muscle stimulation therapy method produces a first series of pulses and a second series of pulses, and adjusting the voltage of at least one of the first series of pulses and the second series of pulses based on said voltage adjustment to thereby control the output current level below a maximum threshold.

It is an object of the present invention to provide an electrical muscle stimulation therapy method, wherein various impedance values, comparison values, and actions to be taken are displayed.

It is an object of the present invention to provide an electrical muscle stimulation therapy method, wherein the electrical muscle stimulation therapy apparatus produces a first series of pulses and said second series of pulses that are automatically adjusted based on measured impedance values.

SUMMARY OF THE INVENTION

In accordance with one aspect of the present invention there is disclosed a novel method of treating a patient, the method comprising the steps of generating a first series of pulses having a frequency in a range from about 1 Hz to about 5 kHz, a voltage range from about 0 (zero) volts to about 100 (one hundred) volts, and a duty cycle of about 1% to about 90%; generating a second series of pulses having a frequency in a range from about 5 kHz to about 50 kHz, a voltage range from about 0 (zero) volts to about 100 (one hundred) volts, and a duty cycle of about 1% to about 90%; modulating the first series of pulses and the second series of pulses into a combined waveform of pulses; and delivering the combined waveform of pulses to the skin of the patient via an electrical circuit to thereby treat the patient.

In accordance with another aspect of the present invention there is disclosed a novel method of treating a patient, the method comprising the steps of generating a first series of pulses; generating a second series of pulses; modulating the first series of pulses and the second series of pulses into a combined waveform of pulses; and delivering the combined waveform of pulses to the skin of the patient via an electrical circuit to thereby treat the patient; monitoring the voltage and the current produced by the electrical circuit to attain a voltage value and a current value; calculating the impedance of the tissue of the patient using the voltage value and the current value; determining a voltage adjustment for at least one of the first series of pulses and the second series of pulses based on the impedance; adjusting the voltage of at least one of the first series of pulses and the second series of pulses based on the voltage adjustment to thereby control the output current level below a maximum threshold.

In accordance with another aspect of the present invention there is disclosed a novel method of treating a patient, the method comprising the steps of generating a first series of pulses; generating a second series of pulses; modulating the first series of pulses and the second series of pulses into a combined waveform of pulses; and delivering the combined waveform of pulses to the skin of the patient via an electrical circuit to thereby treat the patient; monitoring the voltage and the current produced by the electrical circuit to attain a voltage value and a current value; calculating the impedance of the tissue of the patient using the voltage value and the current value; displaying the calculated impedance.

In accordance with another aspect of the present invention there is disclosed a novel method of treating a patient, the method comprising the steps of generating a first series of pulses; generating a second series of pulses; modulating the first series of pulses and the second series of pulses into a combined waveform of pulses; and delivering the combined waveform of pulses to the skin of the patient via an electrical circuit to thereby treat the patient; monitoring the voltage and the current produced by the electrical circuit to attain a voltage value and a current value; calculating the impedance of the tissue of the patient using the voltage value and the current value; converting the calculated impedance to an impedance factor; and displaying the impedance factor.

In accordance with another aspect of the present invention there is disclosed a novel method of treating a patient, the method comprising the steps of generating a first series of pulses; generating a second series of pulses; modulating the first series of pulses and the second series of pulses into a combined waveform of pulses; and delivering the combined waveform of pulses to the skin of the patient via an electrical circuit to thereby treat the patient; monitoring the voltage and the current produced by the electrical circuit to attain a voltage value and a current value; calculating the impedance of the tissue of the patient using the voltage value and the current value; calculating an impedance value related to the calculated impedance; and displaying the impedance value and a benchmark impedance value for comparison purposes.

In accordance with another aspect of the present invention there is disclosed a novel method of treating a patient, the method comprising the steps of generating a first series of pulses; generating a second series of pulses; modulating the first series of pulses and the second series of pulses into a combined waveform of pulses; and delivering the combined waveform of pulses to the skin of the patient via an electrical circuit to thereby treat the patient; monitoring the voltage and the current produced by the electrical circuit to attain a voltage value and a current value; calculating the impedance of the tissue of the patient using the voltage value and the current value; calculating an impedance value related to the calculated impedance; calculating a comparison value based on the impedance value and a benchmark impedance value; and displaying the comparison value.

In accordance with another aspect of the present invention there is disclosed a novel method of treating a patient, the method comprising the steps of generating a first series of pulses; generating a second series of pulses; modulating the first series of pulses and the second series of pulses into a combined waveform of pulses; and delivering the combined waveform of pulses to the skin of the patient via an electrical circuit to thereby treat the patient; monitoring the voltage and the current produced by the electrical circuit to attain a voltage value and a current value; calculating the impedance of the tissue of the patient using the voltage value and the current value; calculating an impedance value related to the calculated impedance; determining an action to be taken based on the impedance value and a benchmark impedance value; and displaying the action to be taken.

In accordance with another aspect of the present invention there is disclosed a novel method of treating a patient, the method comprising the steps of generating a first series of pulses; generating a second series of pulses; modulating the first series of pulses and the second series of pulses into a combined waveform of pulses; and delivering the combined waveform of pulses to the skin of the patient via an electrical circuit to thereby treat the patient; monitoring the voltage and the current produced by the electrical circuit to attain a voltage value and a current value; calculating the impedance of the tissue of the patient using the voltage value and the current value; calculating an impedance value related to the calculated impedance; automatically adjusting the first series of pulses and the second series of pulses based on the impedance value.

In accordance with another aspect of the present invention there is disclosed a novel method of treating a patient, the method comprising the steps of generating a first series of pulses; generating a second series of pulses; modulating the first series of pulses and the second series of pulses into a combined waveform of pulses; and delivering the combined waveform of pulses to the skin of the patient via an electrical circuit to thereby treat the patient; monitoring the voltage and the current produced by the electrical circuit to attain a voltage value and a current value; calculating the impedance of the tissue of the patient using the voltage value and the current value; calculating an impedance value related to the calculated impedance; determining an action to be taken based on the impedance value and a benchmark impedance value; and automatically adjusting the first series of pulses and the second series of pulses based on the action to be taken.

Other advantages, features and characteristics of the present invention, as well as methods of operation and functions of the related elements of the structure, and the combination of parts and economies of production, will become more apparent upon consideration of the following detailed description and the appended claims with reference to the accompanying drawings, the latter of which is briefly described herein below.

BRIEF DESCRIPTION OF THE DRAWINGS

The novel features which are believed to be characteristic of the method of treating a patient and apparatus therefor, together with further objectives and advantages thereof, will be better understood from the following drawings in which a presently preferred embodiment of the invention will now be illustrated by way of example. It is expressly understood, however, that the drawings are for the purpose of illustration and description only, and are not intended as a definition of the limits of the invention. In the accompanying drawings.

DETAILED DESCRIPTION OF THE ILLUSTRATED EMBODIMENT

Reference will now be made to FIGS. 1 through 7, which show an illustrated embodiment of the method of treating a patient and apparatus therefor according to the present invention.

Figure 4:
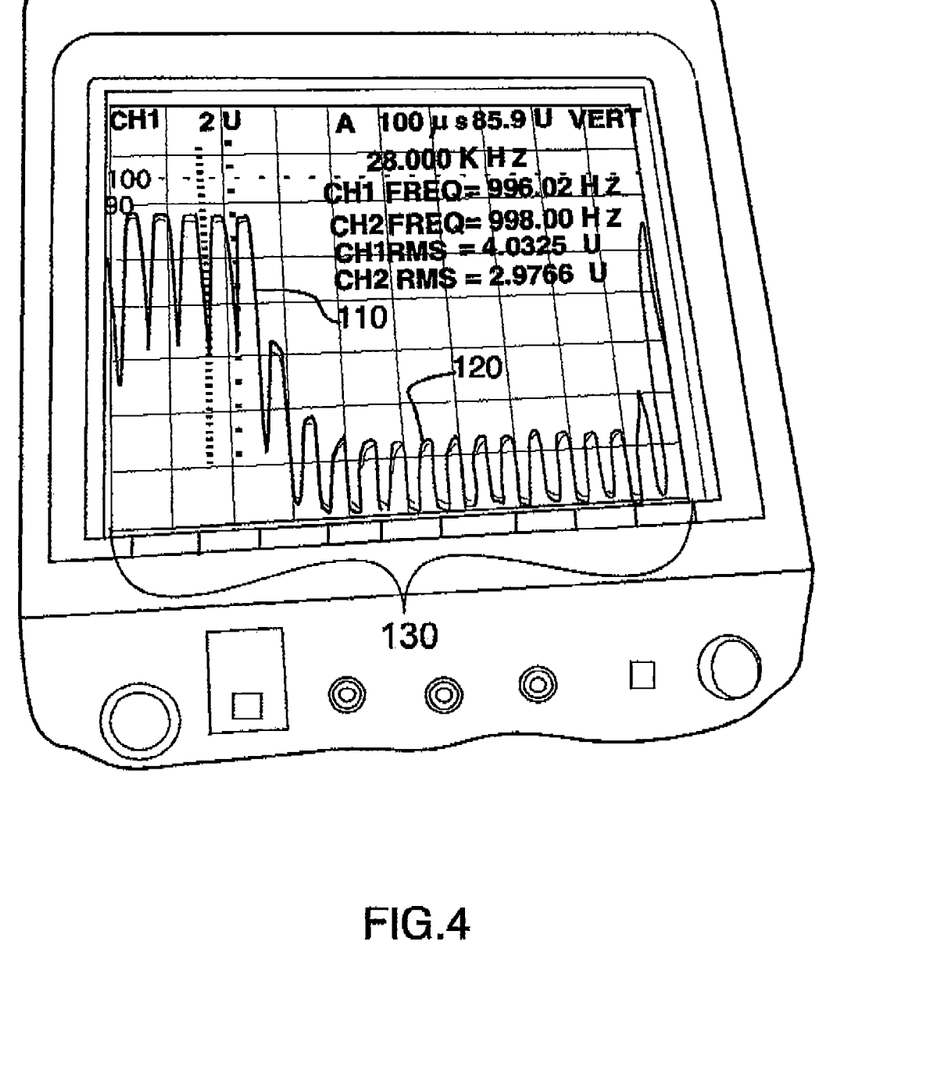
FIG. 4 is a scan on an oscilloscope showing the first series of pulses and the second series of pulses.

In one aspect, the present invention comprises a novel method of treating a patient 109. The method comprises the steps of generating a first series of pulses 110 and generating a second series of pulses 120. In the present invention, a signal generating apparatus 100 is used. In the disclosed embodiment, the first series of pulses 110 has a frequency in a range from about 1 Hz to about 5 kHz, a voltage range from about 0 (zero) volts to about 100 (one hundred) volts, and a duty cycle of about 1 to about 90%. The second series of pulses 120 has a frequency in a range from about 5 kHz to about 50 kHz, a voltage range from about 0 (zero) volts to about 100 (one hundred) volts, and a duty cycle of about 1% to about 90%. The method also includes the step of modulating the first series of pulses 110 and the second series of pulses 120 into a combined waveform of pulses 130, as shown in FIG. 4. Subsequently to modulating the first series of pulses 110 and the second series of pulses 120, the combined waveform of pulses 130 is delivered to the skin of the patient 109 via an electronic circuit to thereby treat the patient 109. In the disclosed embodiment, the electronic circuit may comprise a first pair of electrodes (first electrode pad 141 and second electrode pad 142) and a second pair of electrodes (third electrode pad 143 and fourth electrode pad 144). The first pair of electrodes is attached in electrically conductive relation to a patient's skin at a first area. Similarly, the second pair of electrodes is attached in electrically conductive relation to a patient's skin at a second area. The output, or in other words the combined waveform of pulses 130, from the first pair of electrodes is the same as the output from the second pair of electrodes. Further, the output, or in other words the combined waveform of pulses 130, from the first electrode pad 141 is typically the same waveform as the output from the third electrode pad 143, and the output, or in other words the combined waveform of pulses 130, from the second electrode pad 142 is typically the same waveform as the output from the fourth electrode pad 144; however, it is common to have the amplitude different one pair of electrodes from the other.

It has been found that in order to properly combine the first series of pulses 110 and the second series of pulses 120 into a steady combined waveform of pulses 130 that does not shift significantly, the frequency of the first series of pulses 110 should be an integer multiple of the frequency of the second series of pulses 120.

Figure 3:
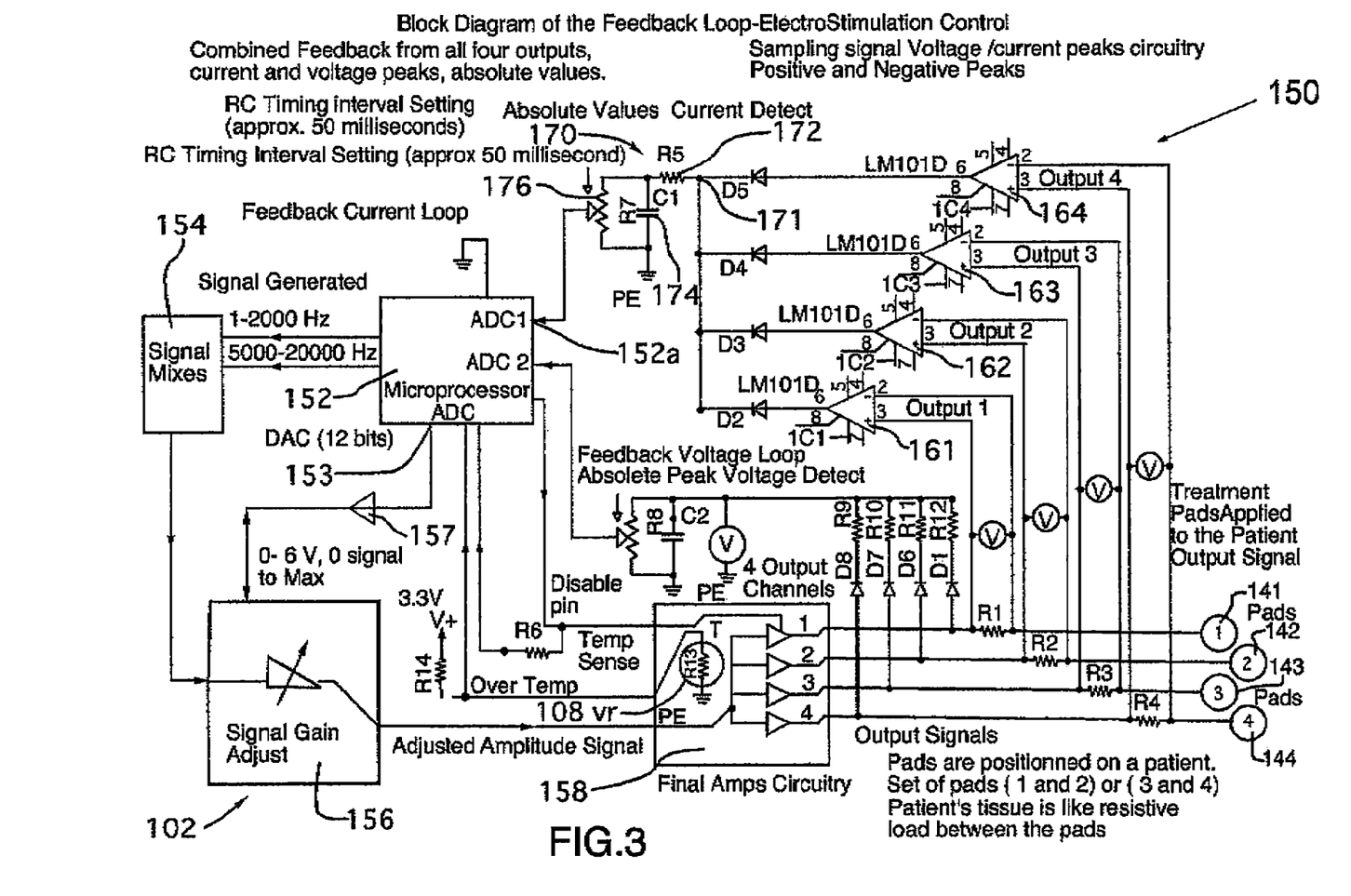
FIG. 3 is an electrical schematic that is representative of the apparatus and method according to the present invention of FIG. 1, and showing a representation of a combined waveform of pulses used to treat a patient.

The present invention also includes step of monitoring the voltage and the current produced by the electronic circuit to attain a voltage value and a current value. The voltage and current values that are produced by the electronic circuit 102 of the apparatus 100 according to the present invention are measured and used by the electronic circuit 102 itself via feedback loop current circuit 170. Further, the voltage and current values are measured at a point in time, and may be measured as frequently as desired. Also, the voltage and current values are measured with respect to first electrode pad 141 and the second electrode pad 142, and also are measured between the third electrode pad 143 and the fourth electrode pad 144, to thereby produce the measured voltage and current values.

Subsequent to measuring the voltage values and current values, the step of calculating the impedance of the tissue of the patient 109 using the voltage value and the current value is performed. The calculated impedance is indicative of the impedance, or other words resistance, to electrical flow of the tissue of the patient 109 between the electrodes.

The next step is that of determining a voltage adjustment for at least one of the first series of pulses 110 and the second series of pulses 120 based on the impedance. Since the first series of pulses 110 and the second series of pulses 120 have been modulated together to form a combined waveform of pulses 130, the measurement of is the maximum voltage of the combined waveform. It has been found that the frequency may be adjusted within a range from about 1 Hz to about 5 kHz, the voltage may be adjusted within a range from about 0 (zero) volts to about 100 (one hundred) volts, and the duty cycle may be adjusted within a range of about 1% to about 90%. The voltage is measured peak-to-peak and therefore ranges from +50 volts to −50 volts).

If desired, the next step may be that of automatically adjusting the voltage of at least one of the first series of pulses 110 and the second series of pulses 120 based on the voltage adjustment that has been determined. Such automatic adjustment of the voltage of at least one of the first series of pulses 110 and the second series of pulses 120 is performed to thereby control the output current level below a maximum threshold. In the present invention, the step of monitoring the voltage across the pair of electrodes and the current through the pair of electrodes is performed at a time interval of about between about 10 ms and 100 ms, and even more specifically is performed at a time interval of about 50 ms.

Further, the step of adjusting the voltage of at least one of the first series of pulses 110 and the second series of pulses 120 according to the calculated impedance to thereby control the output current level below a maximum threshold may comprise adjusting the voltage of the first series of pulses 110 according to the calculated impedance to thereby control the output current level below a maximum threshold. Alternatively or additionally, the step of adjusting the voltage of at least one of the first series of pulses 110 and the second series of pulses 120 according to the calculated impedance to thereby control the output current level below a maximum threshold may comprise adjusting the voltage of the second series of pulses 120 according to the calculated impedance to thereby control the output current level below a maximum threshold. Also, the step of adjusting the voltage of at least one of the first series of pulses 110 and the second series of pulses 120 according to the calculated impedance to thereby control the output current level below a maximum threshold may comprise adjusting the voltage of both the first series of pulses 110 and the second series of pulses 120 according to the calculated impedance to thereby control the output current level below a maximum threshold.

It has been determined through experimentation that the step of adjusting the voltage of at least one of the first series of pulses 110 and the second series of pulses 120 according to the calculated impedance to thereby control the output current level below a maximum threshold may advantageously comprise reducing the voltage by about 5% of at least one of the first series of pulses 110 and the second series of pulses 120 according to the calculated impedance to thereby control the output current level below a maximum threshold.

It is further contemplated that the step of adjusting the frequency of the first series of pulses 110 may comprise adjusting the frequency of one or both of the first series of pulses 110 and the second series of pulses 120 according to the calculated impedance.

Figure 5:
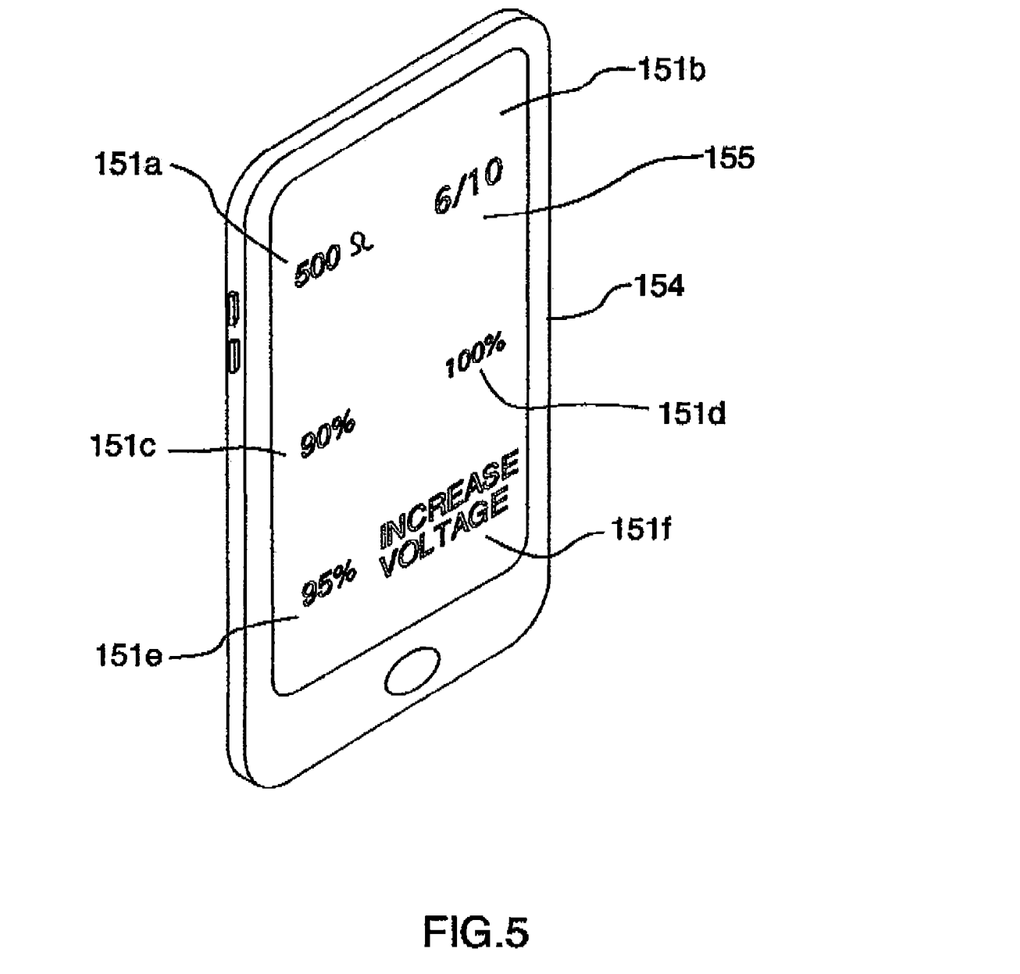
FIG. 5 is a front plan view of a cellular telephone connected in data transfer relation to the apparatus of FIG. 1, and displaying a calculated impedance, an impedance factor, an impedance value, a benchmark impedance value, a comparison value and an action to be taken.

It has also been found that in the present invention, communicating the results of the impedance values that are determined by the measurements of the voltage and current at the output of the electronic circuit according to the present invention is of significance. Accordingly, an important step in the method of the present invention comprises displaying the calculated impedance 151a, such as on a digital display 104 on the apparatus 100. The calculated impedance is expressed in ohms and is derived by dividing the voltage by the current. A person knowledgeable in this art, or generally knowledgeable in the art of electronics, may be comfortable with dealing with a displayed impedance value expressed in ohms; however, in the present invention, the method according to the present invention may further comprise the step of converting the calculated impedance to an impedance factor 151b. Further, there may be the step of displaying the impedance factor 151b. The impedance factor 151b may be expressed on a scale such as a cardinal scale of 1 (one) to 10 (ten), or similar, or any other convenient scale or the like that would be meaningful to a technician or a patient 109.

Further, a maximum impedance factor and/or a minimum impedance factor may be displayed. The maximum impedance factor might represent the maximum desired impedance of the muscle tissue and the minimum impedance factor might represent the minimum desired impedance of the muscle tissue. Encountering measured impedance factors outside of the range of the maximum impedance factor and the minimum impedance factor can indicate potential problems with the cells of the muscle tissue.

A desired impedance factor might also be displayed. The desired impedance factor could be a guide to perhaps an ideal physiological condition of the cells of the muscle tissue being treated, and could be used as a guide as to whether the treatment is helping the cells with the muscle tissue.

A target impedance factor might also be displayed. The target impedance factor could be a temporary target value or a final targeted value that is trying to be reached given the type of muscle tissue being treated and information about the possible injuring or illness.

A standardized impedance factor might also be displayed. The standardized impedance factor could be an impedance factor that is accepted in the physiological treatment profession as being a value that my general would be expected for the particular treatment in that particular area of the human body, possibly also considering given the conditions that are being encountered.

Further, the present invention might include the steps of calculating an impedance value 151c related to the calculated impedance, and also displaying the impedance value 151c and a benchmark impedance value for comparison purposes. The impedance value and a benchmark impedance value 151d might be expressed in physiologically related terms, such as oxygen saturation in cells, protein levels in cells, and so on. A benchmark impedance value 151d is may be defined as a standard of excellence, achievement, and so on, against which similar things may be measured or judged.

Additionally, the steps of calculating a comparison value 151e based on the impedance value and the benchmark impedance value 151d, and displaying the comparison value could be performed in order to qualitatively and/or quantitatively relate the impedance value and the benchmark impedance value in a manner that is meaningful and can be readily understood by a technician, a patient 109, or the like.

Also, the steps of determining an action to be taken 151f based on the impedance value and the benchmark impedance value, and displaying the action to be taken 151f can be performed. The displayed action may comprises reducing or increasing voltage of at least one of the first series of pulses 110 and the second series of pulses 120. Alternatively or additionally, the steps of calculating an impedance value related to the calculated impedance and automatically adjusting the first series of pulses 110 and the second series of pulses 120 based on the impedance value could be performed in order to provide automatic adjustment of the pulse is provided to the patient 109, thereby helping to optimize the treatment. The step of automatically adjusting the first series of pulses 110 and the second series of pulses 120 based on the impedance value could comprise automatically adjusting at least one of the frequency, the duty cycle and the voltage of the first series of pulses 110 and the second series of pulses 120. Further an electrical current value within a desired range or within a pre-determined range could be selected.

Also or additionally, the present invention could include the steps of calculating an impedance value related to the calculated impedance and determining an action to be taken based on the impedance value and a benchmark impedance value, and automatically adjusting the first series of pulses 110 and the second series of pulses 120 based on the action to be taken. For instance, the action to be taken could be to decrease the voltage by 10% and slowly increase the voltage incrementally to see what resulting impedance is produced.

Figure 6:
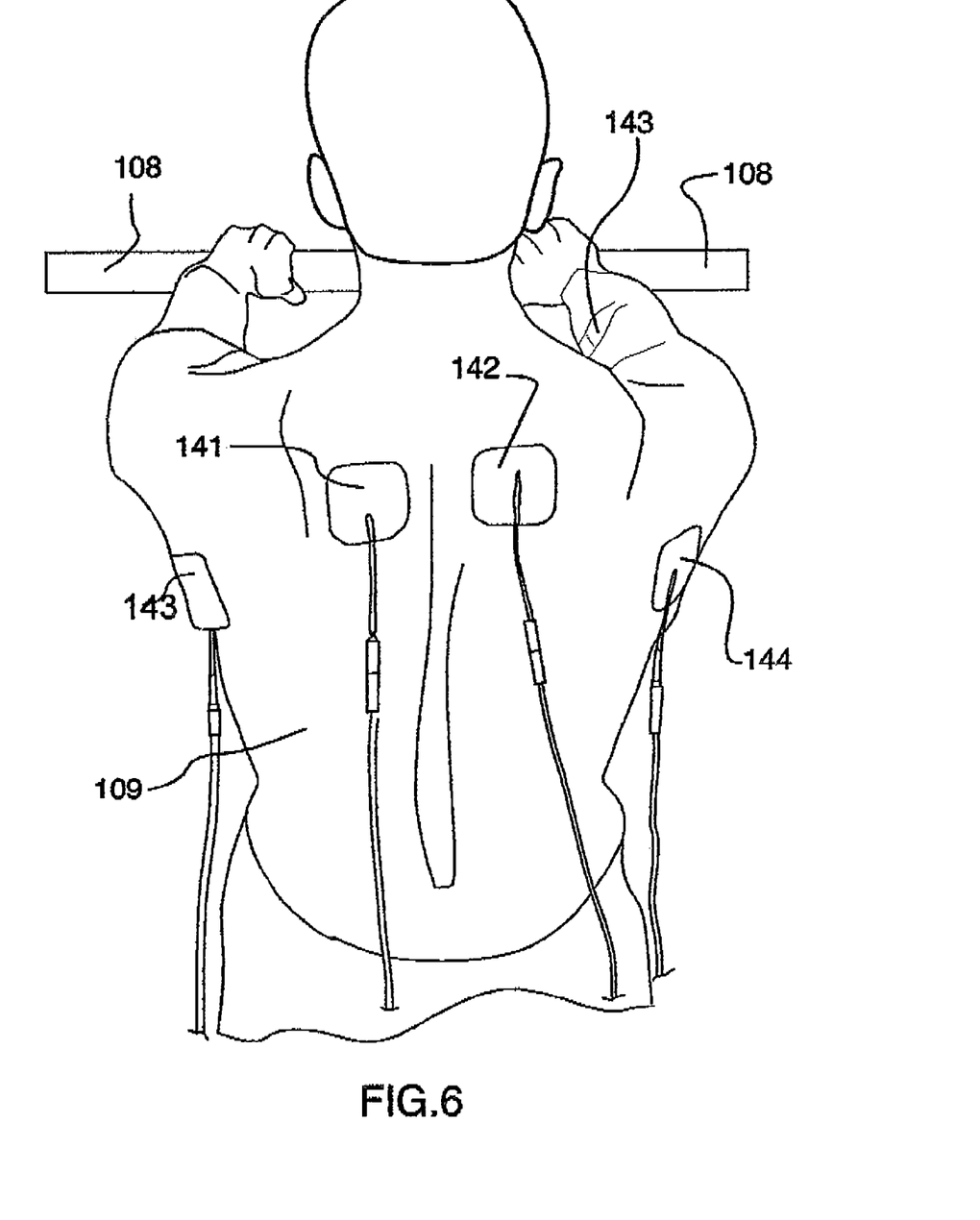
FIG. 6 is a perspective view from the side of the apparatus according to the present invention connected to a patient for providing treatment, and with the patient holding the horizontal stability post; and, FIG. 7 is an enlarged top plan view of a portion of the rotary dial mounted on the horizontal stability post, and showing the patient using one hand to adjust the rotary dial.
Figure 7:
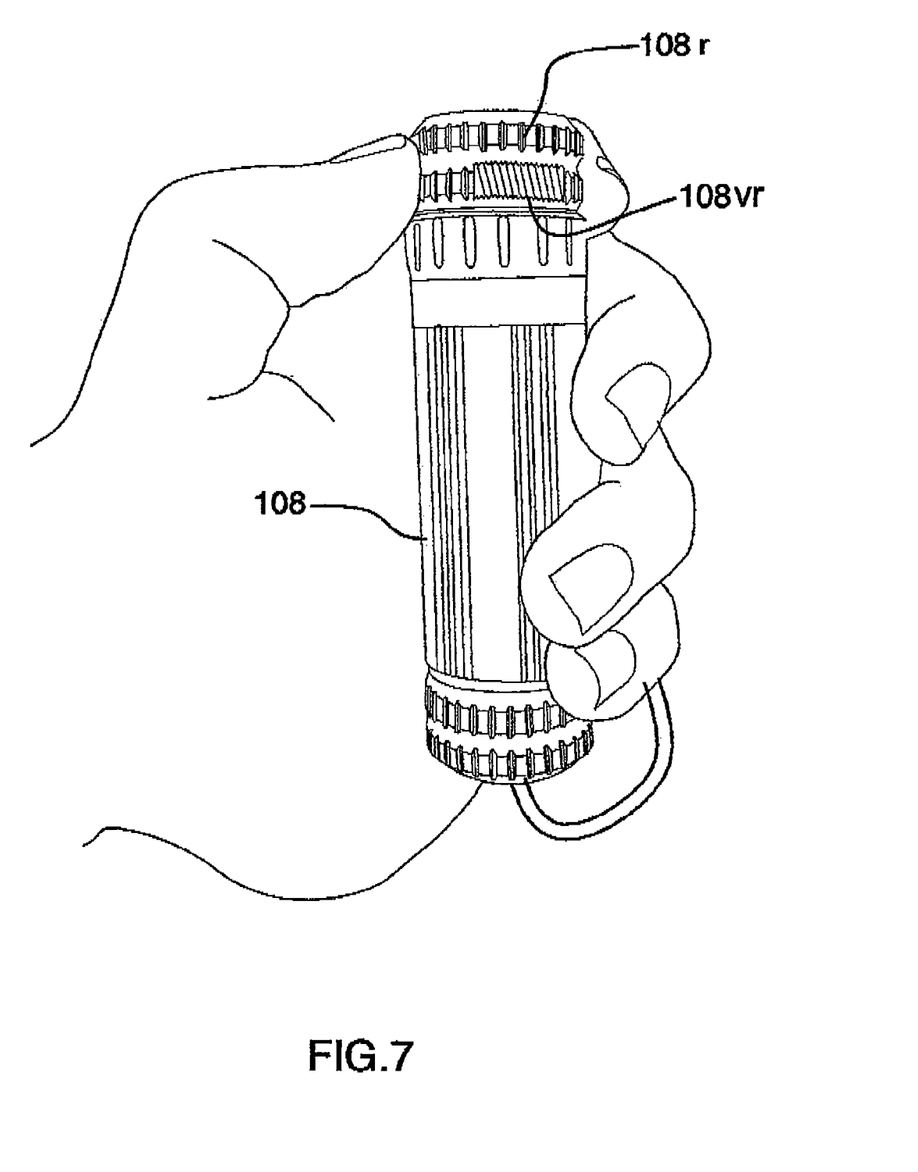

Reference will now be made to FIGS. 5 through 7, which show the apparatus according to the present invention in use. The first electrode pad 141, the second electrode pad 142, the third electrode pad 143 and the fourth electrode pad 144 are secured in electrically conductive relation to the patient's skin. Also, a horizontal stability post 108 is gripped by the patient 109 in order to help the patient 109 have proper upright posture that is literally even, and also to indicate when the patient's posture might become improper or uneven. The apparatus can readily be used to properly treat the patient 109 according to the method of the present invention.

Reference will now be made to FIG. 3, which shows the electrical schematic that is representative of the circuit 150 that is the basis of the apparatus 100 and method according to the present invention. The microprocessor 152 that is used is a STM32 produced by ST Microelectronics, part number F303K8. Any suitable microprocessor 152 could alternatively be used. The microprocessor 152 is programmed to generate the first series of pulses 110 and the second series of pulses 120 that have the various voltage, frequency and duty cycle characteristics as set forth above.

Figure 1:
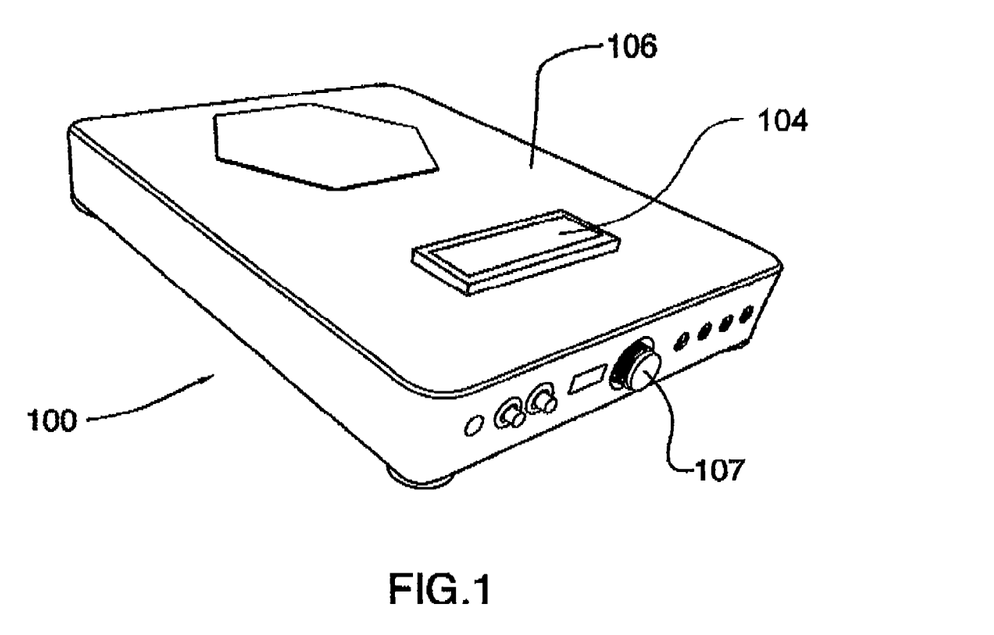
FIG. 1 is a side elevational view of the apparatus according to the present invention.
Figure 2:
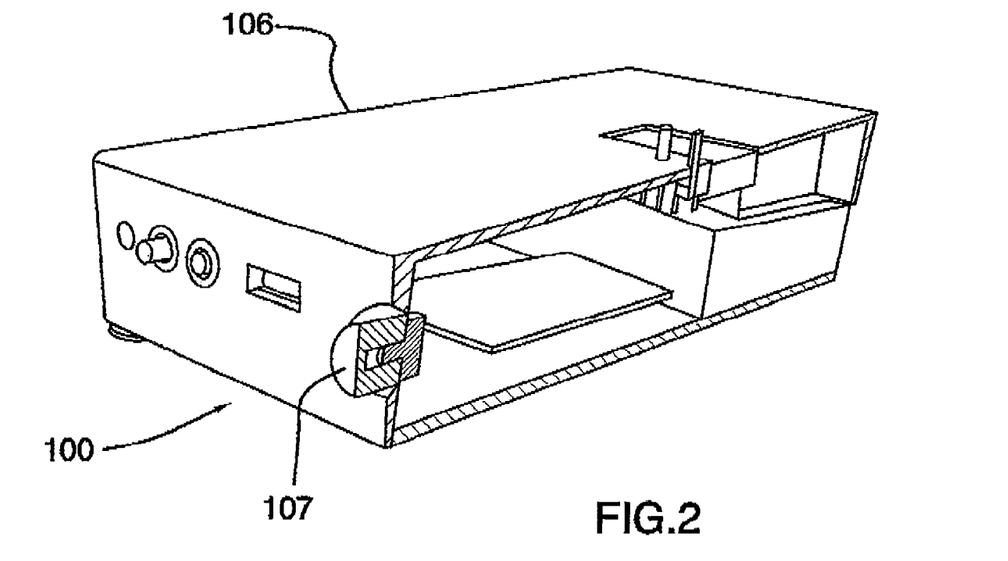
FIG. 2 is a cut-away perspective view of the apparatus of FIG. 1.

The first series of pulses 110 and the second series of pulses 120 are modulated in the mixer circuitry 154 to thereby form the combined waveform of pulses 130, which is fed into a signal gain adjust circuit 156. The signal gain adjust circuit 156 is used to permit selective adjustment of the voltage level of the first series of pulses 110 and the second series of pulses 120. This adjustment can be made by a technician or by the patient 109. in the main illustrated embodiment, as can be seen in FIGS. 1 and 2, this adjustment can be made by turning the adjustment knob 107 on the main housing 106 of the apparatus 100 according to the present invention. Alternatively, as can be seen in FIG. 7, a rotary dial 108r of one end of the horizontal stability post 108 turns a variable resistor 108vr, or the like. The variable resistor is connected in electrically conductive relation to the signal gain adjust circuit 156 to allow for adjustment of the voltage level of the first series of pulses 110 and the second series of pulses 120 of the combined waveform of pulses 130 via the rotary dial.

The microprocessor 152 also feeds a DC voltage through a doubling amplifier 157 into the signal gain adjust circuit 156 in order to control the amplitude of the output waveform. The output of the signal gain adjust circuit 156 is fed into a final amplifier 158 having four output channels. Each of the four output channels is fed through a separate resistor (R1,R2,R3,R4) to a corresponding electrode pad, namely first electrode pad 141, a second electrode pad 142, a third electrode pad 143, and a fourth electrode pad 144. The four electrode pads are each placed securely in electrically conductive relation to the skin of a patient 109 at the area to be treated. The combined waveform of pulses 130 created from the first series of pulses 110 and the second series of pulses 120 is fed through the four electrode pads. The combined waveform of pulses 130 is present across the first electrode pad 141 and second electrode pad 142, and similarly is present across the third electrode pad 143 and fourth electrode pad 144.

As is discussed above, the impedance of the tissue of the patient 109 between the first electrode pad 141 and the second electrode pad 142 and also between the third electrode pad 143 and fourth electrode pad 144 voltage by the current can be calculated by dividing the voltage by the current. The voltage output of the first electrode pad 141 and the second electrode pad 142 is determined. Similarly, the voltage output of the third electrode pad 143 in the fourth electrode pad 144 is determined.

More specifically, at each of the four outputs of the final amplifier 158, there is a resistor (R1,R2,R3,R4) that in the present circuit have a value of ten (10) ohms. The voltage across R1 leading to the first electrode pad 141 is fed back into the inputs of a first operational amplifier 161. Similarly, the voltage across R2 leading to the second electrode pad 142 is fed back into the inputs of a second operational amplifier 162, the voltage across R3 leading to the third electrode pad 143 is fed back into the inputs of a third operational amplifier 163, and the voltage across R4 leading to the fourth electrode pad 144 is fed back into the inputs of a fourth operational amplifier 164. The outputs of the four operational amplifiers are fed through diodes to a common input 171 of a feedback loop current circuit 170, specifically through a resistor 172, to act on the capacitor 174. The voltage across capacitor 174 changes as the voltages from the operational amplifiers change. Basically, the resistor 172 and the capacitor 174 act to "smooth out" the peak voltages so that extreme variations of the voltage do not affect the feedback operation of the overall electronic circuit 102.

The voltage across the capacitor 174 is applied as an absolute value into a first input 152*a* of the microprocessor 152. If the voltage received by the first input 152*a* of the microprocessor 152 increases greater than a threshold amount, the microprocessor 152 decreases the voltage of the first series of pulses 110 and/or the second series of pulses 120 by about 5%. The variable resistor 176 is used to calibrate the feedback loop current circuit 170.

The feedback loop current circuit 170 detects absolute value current peaks and absolute value peak voltage peaks of each of the first electrode pad 141, the second electrode pad 142), the third electrode pad 143 and the fourth electrode pad 144. The feedback loop current circuit 170 feeds the voltage values to the microprocessor 152 through pins ADC1 and ADC2. The feedback values are read by the microprocessor 152 at intervals as programmed into the microprocessor 152. The voltage is held by the feedback loop current circuit 170 until read by the microprocessor 152.

As can be readily seen, the electronic circuit 102 according to the present invention employees DC coupled amplifiers to thereby faithfully produce an output that is a combined waveform of pulses. The DC coupled amplifiers accurately and faithfully produce all of the pulse frequencies including 1 Khz to 50 Khz. The known prior art cannot do this since it uses an output transformer that by its very nature can produce signals only in a somewhat narrow range.

The microprocessor 152 evaluates the input absolute values from the feedback loop current circuit 170. If the peak current equals or surpasses the peak limit of 100 mA, the microprocessor 152 is instructed to reduce the DAC value output. 100 mA is the regulated maximum safety level current value. The DAC output pin 153 (12 bits) controls the mixed signal wave voltage amplitude level, from zero to a maximum signal. The DAC values are referenced by voltage levels, between 0 and 6 volts.

The microprocessor 152 may also send message to the APP controller 155 running on a cellular telephone 154 (FIG. 5), or a portable tablet type computer, to limit the upper values being sent to the device, and prompt the user to scale back the sent values.

The microprocessor 152 can also disable the final amplifier 158 if there is a safety condition unmet, depending on the feedback conditions, including temperature sensing.

The microprocessor 152 can also monitor the calibration limits of the electronic circuit 102. A message may also be sent to the APP controller 155 running on a cellular telephone 154, if the electronic circuit 102 is out of calibration. The electronic circuit 102 as illustrated has the following calibration limit conditions:

25% of Amplitude=V25=X value+/−10%
50% of Amplitude=V50=Y value+/−10%
75% of Amplitude=V75=Z value+/−10%

Other variations of the above principles will be apparent to those who are knowledgeable in the field of the invention, and such variations are considered to be within the scope of the present invention. Further, other modifications and alterations may be used in the present invention without departing from the spirit and scope of the accompanying claims.

The invention claimed is:

1. An electrical stimulation apparatus comprising:
   a pulse generator circuit portion including at least a microprocessor configured to generate at least a first series of pulses and a second series of pulses, the first series of pulses having a frequency in a range from 1 Hz to 5 kHz and a voltage range from above 0 (zero) volts to 100 (one hundred) volts, and the second series of pulses having a frequency in a range from 5 kHz to 50 kHz and a voltage range from about 0 (zero) volts to about 100 (one hundred) volts;
   a modulator circuit portion for modulating the first series of pulses and the second series of pulses into a combined waveform of pulses having an amplitude;
   a gain adjust circuit portion for receiving the combined waveform of pulses and permitting the selective adjustment of the amplitude of the combined waveform of pulses;
   a control circuit portion for controlling the gain adjust circuit portion and for controlling the frequency of the first series of pulses and the second series of pulses;
   an amplifier circuit portion for amplifying the combined waveform of pulses received from the gain adjust circuit portion, and having an output circuit portion comprising a plurality of output channels;
   a load engaging portion comprising a plurality of electrodes each connected in signal receiving relation to one of said output channels, for receiving the combined waveform of pulses from the amplifier circuit portion and delivering the combined waveform of pulses to a load;
   a feedback signal generating portion comprising a plurality of resistors of known impedance, with said resistors each disposed between one of said output channels and the corresponding electrode, for generating feedback signals received through the body of a person from the output circuit portion of the amplifier circuit portion;

a feedback circuit portion comprising a plurality of amplifiers, with an input of each amplifier operatively connected across a respective one of said resistors for receiving feedback signals from the respective resistor so as to sense a voltage drop across that respective resistor, to thereby provide feedback based on said first series of pulses and said second series of pulses to preclude output current from the output circuit portion from going above a maximum current; and a final amplifier circuit having four output channels, each output channel being fed through a separate resistor to a corresponding electrode in the load engaging portion and each of the four output channels additionally being fed into the inputs of four operational amplifiers.

2. The electrical stimulation apparatus according to claim 1, wherein said first series of pulses has a duty cycle of 1% to 90%, and said second series of pulses has a duty cycle of 1% to 90%.

3. The electrical stimulation apparatus according to claim 1, wherein said feedback circuit portion further comprises a feedback loop current circuit that receives the feedback signals from the feedback signal generating portion.

4. The electrical stimulation apparatus according to claim 3, wherein outputs of said amplifiers are connected to a common input of the feedback loop current circuit.

5. The electrical stimulation apparatus according to claim 1, wherein said load engaging portion receives the combined waveform of pulses from the amplifier circuit portion and delivers the combined waveform of pulses to said load without passing the combined waveform of pulses through a transformer.

6. The electrical stimulation apparatus according to claim 1, wherein said pulse generator circuit portion comprises the microprocessor and related software.

7. The electrical stimulation apparatus according to claim 1, wherein said modulator circuit portion comprises a signal mixer.

8. The electrical stimulation apparatus according to claim 1, wherein said control circuit portion for controlling the gain adjust circuit portion and for controlling the frequency of the first series of pulses and the second series of pulses comprises the microprocessor and related software.

9. The electrical stimulation apparatus according to claim 1, wherein said amplifier circuit portion comprises a DC-coupled amplifier circuit portion.

10. The electrical stimulation apparatus according to claim 1, wherein said load engaging portion further comprises a plurality of electrode pads.

11. The electrical stimulation apparatus according to claim 1, wherein the frequency of the second series of pulses is an integer multiple of the frequency of the first series of pulses.

12. The electrical stimulation apparatus according to claim 1 further comprising a display screen, the apparatus being configured to display at least one of a maximum impedance factor, a minimum impedance factor, a desired impedance factor, a target impedance factor, and a standardized impedance factor.

13. The electrical stimulation apparatus according to claim 6, wherein the microprocessor is further configured to evaluate the feedback signals and reduce the voltage of the first series of pulses or the second series of pulses by 5% if the voltage of the first series of pulses or the second series of pulses reaches a maximum threshold.

14. The electrical stimulation apparatus according to claim 1, wherein each output from each of the four operational amplifiers are further fed through diodes to a common input of a feedback loop current circuit.

15. The electrical stimulation apparatus according to claim 14, wherein the feedback loop current circuit includes at least a variable resistor and capacitor in parallel configuration.

* * * * *